(12) United States Patent
Crosato

(10) Patent No.: US 9,873,903 B2
(45) Date of Patent: Jan. 23, 2018

(54) METHOD FOR DETERMINING THE STATE OF FERMENTATION PROGRESS OF AN ORGANIC MATERIAL INSIDE A FERMENTER AND A FERMENTER FOR IMPLEMENTING THE METHOD

(71) Applicant: NOFORM SRL, Meolo (VE) (IT)

(72) Inventor: Remo Crosato, Meolo (IT)

(73) Assignee: NOFORM SRL, Meolo (VE) (IT)

( * ) Notice: Subject to any disclaimer, the term of this patent is extended or adjusted under 35 U.S.C. 154(b) by 956 days.

(21) Appl. No.: 14/075,721

(22) Filed: Nov. 8, 2013

(65) Prior Publication Data

US 2014/0134663 A1    May 15, 2014

(30) Foreign Application Priority Data

Nov. 9, 2012 (IT) .............................. TV2012A0212

(51) Int. Cl.
| | |
|---|---|
| *G01N 33/48* | (2006.01) |
| *C12Q 1/02* | (2006.01) |
| *C12M 1/34* | (2006.01) |
| *C12M 1/36* | (2006.01) |

(52) U.S. Cl.
CPC ................ *C12Q 1/02* (2013.01); *C12M 41/32* (2013.01); *C12M 41/34* (2013.01); *C12M 41/48* (2013.01)

(58) Field of Classification Search
CPC ....................................................... C12M 41/32
USPC ............................................................ 702/19
See application file for complete search history.

(56) References Cited

U.S. PATENT DOCUMENTS

2009/0048816 A1* 2/2009 Srinivasa ............... C12M 41/48
703/11

* cited by examiner

*Primary Examiner* — Jerry Lin
(74) *Attorney, Agent, or Firm* — Birch, Stewart, Kolasch & Birch, LLP

(57) ABSTRACT

A method performed by a computer or microprocessor to determine the fermentation progress of an organic material, contained in a container and capable of generating fermentation gas, includes the steps of measuring the amount of gas actually generated over time by the material and determining the state of fermentation progress by comparing said amount with an estimate of the total gas producible by material throughout its fermentation.

10 Claims, 1 Drawing Sheet

Figure 1:
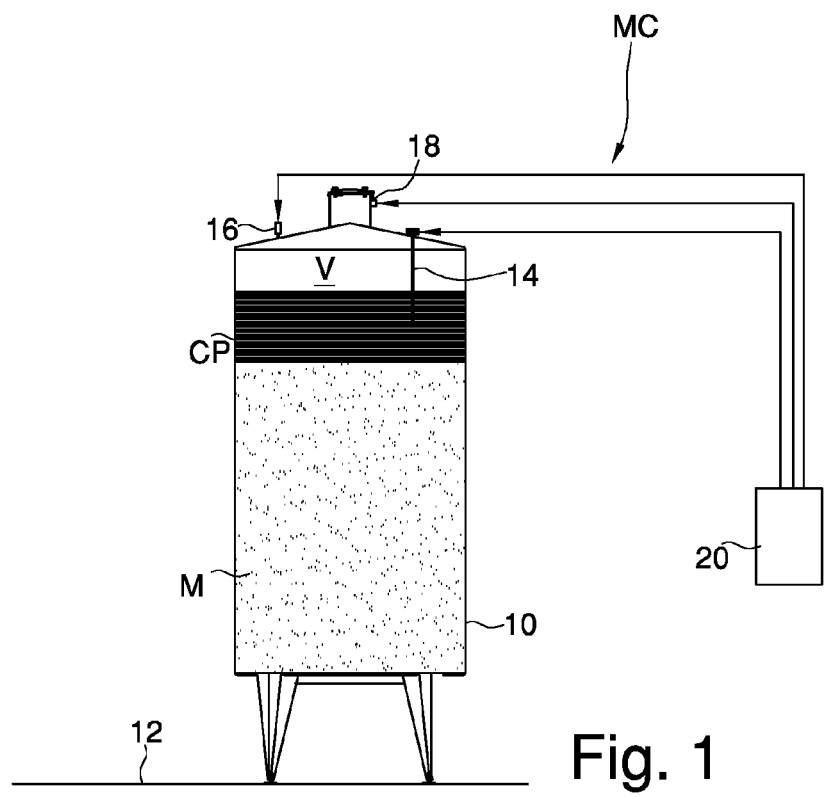

METHOD FOR DETERMINING THE STATE OF FERMENTATION PROGRESS OF AN ORGANIC MATERIAL INSIDE A FERMENTER AND A FERMENTER FOR IMPLEMENTING THE METHOD

The invention relates to a method for determining the state of fermentation progress of an organic material inside a fermenter, and to an improved fermenter implementing the method. In particular, the method is applied to a crushed vegetable material (e.g. must), and the fermenter is a winemaker apparatus for must chosen here as an example.

The alcoholic fermentation of a mass of crushed grapes takes place in an irregular and sometimes tumultuous manner. In his progress it has some well-defined and different phases, which require external intervention usually performed by the oenologist to improve and adjust the fermentation, and thus the final wine.

In addition to the irregularities in the fermentation even arrests can occur, with deleterious effects on the entire fermentation process. These arrests are difficult to detect, and are normally identified within 12-24 hours of delay during the analysis of the residual sugar level in the fermenting must, which normally is performed every 12-24 hours. Therefore considerable uncertainty follows.

In order to continuously detect the sugar level densimeters immersed in the must are also used, but they give highly inaccurate readings. Indeed the fermentating must, e.g. of red grapes, is a mixture of skins, colloidal substances in suspension and especially $CO_2$ generated by the fermentation process, which determines inaccurate detection. Since the population of fermentative yeast is often unevenly distributed in the fermenter, any local measurement can only cover a limited volume of must.

During fermentation $CO_2$ develops, whose production is directly proportional to the amount of must present and to its sugar content, and to heat, directly proportional to the intensity of the fermentation process.

Since over 30° C. yeasts die, causing harmful fermentation arrests, the temperature of the fermenting mass is checked with one or more temperature probes, inserted at different levels in the must and the cap, and with probes connected to thermoregulation interspaces.

The problems of this control method are essentially two. The first is related to the fact that both the temperature sensors and the thermoregulation interspaces act on and/or are in contact with limited fermenting volumes compared to the total mass. Normally temperature gradients are generated both in the must and in the marc cap. Consequently, the sensors measure distorted temperatures, and the thermoregulation interspaces influence the temperature in wrong volumes.

Even the sugar content of the must can have layers, making its local sampling useless.

Since the only tool that oenologists have to decide what is the optimum temperature to be set, in relation to the supposed stage reached in the wine-making, is the daily analysis of sugar content of the must, it can be understood how random and approximate the process normally used today for regularizing the alcoholic fermentation is.

Thus an improved method or fermenter is needed to achieve in a simple but precise manner a measurement and/or control of the alcoholic fermentation.

To provide such a method or fermenter, in order to solve one of the cited problems, is the main object of what is defined in claim 1, where it is proposed a method (performed e.g. by computer or microprocessor) to determine the state of fermentation progress of an organic material, contained in a container and capable of generating fermentation gas, having the steps of
  measuring the amount of gas actually generated over time by the material;
  determining the state of fermentation progress by comparing (or correlating) said amount with an estimate of the total gas producible from the material throughout its whole fermentation.

The method can envisage to calculate the estimate or receive it as predefined data.

The measurement of the amount of generated gas can be done in any way, e.g. with probes or suitable means. In particular it is advantageous (lower cost and greater simplicity of realization) measuring said amount indirectly and/or as the sum of measured doses of generated gas, preferably also periodically removed from the container to avoid problems of accumulation. Or one can measure a dose through the pressure of the generated gas inside a known volume, e.g. constant, in order to deduce, from the relationship between its pressure and the occupied volume, the number of moles. In alternative to the constant volume one can use a deformable volume, e.g. a bag or membrane that collects the gas to be measured.

In particular, said dose can be measured by arranging that the generated gas
  (i) reaches in the known volume a threshold of maximum pressure and/or
  (ii) invades a deformable volume (preferably of known dimensions), e.g. a bag or membrane.

From the measurement of gas pressure in the known volume one can calculate the moles of gas contained in the known volume.

By knowing the capacity of the deformable volume and/or by measuring the gas flow-rate coming in or out from it (if it is deflated) one can calculate the moles of gas contained therein.

One can use many known volumes and make them fill sequentially with generated gas, or can use a lower number of volumes, at most one, by venting them/it or from time to time by taking some gas away from it/them. In particular, in the known and/or deformable volume, one can get a reduction of gas pressure by moving elsewhere or taking away (outside the known volume and/or the container, e.g. by aspirating the gas) part or all of the gas, and one can calculate such amount or dose as a function of said reduction.

As a function of
  the quantity of material, e.g. the volume of crushed vegetable material inserted into the fermenter before the start of the alcoholic fermentation (and thus, indirectly, the void volume of the upper part of the fermenter), and/or
  its sugar content, e.g. in the must the value of the level of sugar of the grape (measure that is normally carried out in the winery before crushing the grapes), and/or
  the quantity of must present in the entire mass of crushed grapes (every oenologist is able to assess with accuracy of about +/−3% the amount of present must in the processed grape);
one can calculate said estimate, i.e. the total amount of moles of gas or $CO_2$ produced by the material during the entire fermentation process, and from there possibly develop an ideal curve of fermentation. The actual point on this curve, which corresponds to the state of fermentation progress, can be calculated by storing, and/or by adding each time to the preceding ones, the dose of expelled gas from the volume and/or container, so as to determine the total amount of moles of expelled gas from the beginning of the process. By comparing the gas produced up to the present time with the estimated overall fermentation curve one can estimate not only the fermentative course but also the degree of progress achieved on the curve.

Regardless of the means or ways of measurement of said amount, the method can envisage to sample (i.e. obtain a value for) said amount in successive time instants, so as to form a actual time curve of the fermentation, e.g. to be able to compare it with the reference estimated fermentation curve. In particular, to improve the accuracy of the estimate of said amount it is advantageous to perform a thickening of detected samples when it is estimated that the gas production is increasing and/or at a peak. In fact, in the must the alcoholic fermentation, i.e. the transformation of sugars into alcohol, heat and $CO_2$ by yeasts, occurs according to a particular curve that has: an initial, very slow production of $CO_2$, then a phase of tumultuous production and finally a phase of constant reduction of production.

In general a possible further step of the method is to intervene to correct or adjust the progress of fermentation after determining the actual state of fermentation progress. The purpose is to impose to the actual fermentation progress a reference course, which can be the aforementioned calculated ideal curve.

Regardless of the means or ways of measuring said amount, knowing (1b) the ideal or desired fermentation curve or by developing a reference curve, and (2b) the amount of gas or $CO_2$ actually produced by the material, one can act, better if automatically, on the material and/or fermentation to minimize deviations from the reference. By having the previous data (1b) and (2b) it can be known, e.g. for must of grape, both the quantity of actual alcohol (residual sugars) and in which stage the fermentation is.

E.g. as a corrective action on the fermentative course one can adjust the temperature of thermoregulation means or pockets present in the container, or one can oxygenate the mass of the material (e.g. by injecting gas and/or $O_2$), for respectively slowing down or accelerating the fermentation dynamics and get a fermentation as adhering to the set reference as possible.

In addition, one can monitor the fermentation progress in order to immediately detect anomalies, since the fermentative arrests involve abrupt reductions in the production of gas and/or $CO_2$. Or an abnormal or excessive slowdown in the production of gas and/or $CO_2$ can connote suffering of yeasts, which can be reacted to by
  a rise in temperature of the mass of material, and/or
  injection of air/oxygen and/or insertion of nutriments in the mass of material.

By the claimed method one can achieve an accurate control of fermentation, with a precision that can be estimated e.g. between 5% and 10% with regard to the conversion of sugars into alcohol.

One can also continuously display the progress of the fermentation process, e.g. on a graph and/or monitor, e.g. leaving the operator with the responsibility to intervene.

Measuring the amount of gas and/or $CO_2$ actually produced allows to have a data of the total amount of converted sugars, and also solves the problem of accurately analyzing the sugar content. Taking samples of must or material only in a few volumes gives uncertain results, while the proposed method provides a data comprehensive of all the mass of the material, which is considerably more reliable.

To obtain an even more precise data on the production of gas and/or $CO_2$, said amount can be correlated with the fermentation temperature. At higher fermentative temperatures (e.g. between 25° C. and 30° C.) one will have proportionately a higher amount of moles of expelled gas and/or $CO_2$, at lower temperatures (e.g. between 16° C. and 25° C.) there will be proportionately lower numbers of moles of expelled gas and/or $CO_2$.

It may happen that some of the gas expelled from the volume comes from the inside of the material and therefore the measurement of the moles is inaccurate. To improve the accuracy the method can envisage to temporarily isolate the known and/or deformable volume from the container, and then the gas is evacuated from the known and/or deformable volume (e.g. by emptying it from the excess gas). In this way the known and/or deformable volume is decoupled from the material and the expelled or evacuated gas is only that in the known and/or deformable volume.

The method can be performed manually, but it is advantageously executed and/or managed by an electronic unit having e.g. a programmable microprocessor. In particular, every step of the method described before can be implemented and/or carried out by the electronic unit, in particular by having it running a software program adapted to check and/or drive appropriate means, and to make the fermenter described below execute the steps of the method.

Preferably the method is performed by means of a fermenter comprising
  a container for containing an organic material that can generate fermentation gas,
  a volume for containing gas generated from the material, characterized by comprising
  means for detecting the amount of gas actually generated over time by the material in the volume, and
  an electronic processing unit adapted to calculate the progress in fermentation of the material by comparing said amount with an estimate of the gas producible overall by the material throughout its whole fermentation.

The advantages of this apparatus are the same as those of the method, and are not repeated.

In particular the unit for correlating the amount of overall generated gas up to that time can use as an estimate a numerical value or, better, an ideal estimated fermentative curve (set of points) and/or a pre-calculated one and contained in a memory, in order to detect more accurately the stage reached by the fermentation (as explained for the method). Advantageously, the unit can be programmed so that the ideal fermentative curve is programmable, i.e. not derived from the material but set/forced by a user.

The unit can be programmed to
  activate alarm means if it determines anomalies or fermentative arrests, and/or
  perform a series of programmed corrective actions, e.g. by driving thermoregulation means to vary the temperature of the fermentating material, and/or means for performing pumping-overs, and/or means for oxygenating the material, and/or means for pressing the material, etc. The purpose is to bring the actual fermentation closer to the desired, ideal fermentation curve.

The said volume to contain can comprise one or more volumes, to isolate and/or to empty (completely or partially) of the gas they contain.

The means to detect the amount of generated gas can comprise
probes or gas flow meters and/or
a deformable volume or chamber (preferably of known dimensions), e.g. a bag or membrane, in which the generated gas can migrate to then determine the amount thereof, and/or
a known volume or chamber of known size through which to calculate the moles of gas contained therein.

The known volumes can be a plurality, or one or two. One can from time to time vent them/it wholly or in part, or can keep the gas in it/them for a certain time (e.g. to retrieve and exploit it elsewhere), since what counts is only the determination/measurement of said amount (e.g. in moles) of generated gas and not his fate.

In particular it is advantageous (lower costs and greater simplicity of construction) that the means for detecting comprise a sensor, controlled by said control unit, for detecting the gas pressure in the volume. The indirect measurement of the moles via the pressure is simple and inexpensive.

In particular, in the known and/or deformable volume, one can get a decrease in the gaseous pressure by moving part, or all, of the gas outside the known volume and/or the container, and as a function of said decrease a dose of generated gas can be calculated.

To the aim, the fermenter can comprise means for evacuating the gas present in the volume, the means being controlled by said unit in order to evacuate from the volume a known dose of gas. By evacuating or isolating more doses one can then determine the total gas generated up to that oment by summing in the unit the numeric values corresponding to the moles of gas of all the doses.

Not only costly probes are avoided but said dose is calculated by the unit simply with data relating to quantities of the gas, such as volume and pressure.

To improve the accuracy in determining said dose (see the explanation given for the method), in the fermenter said volume can comprise an auxiliary container to contain only gas, and there are
a gas connection between said auxiliary container and said volume;
means controlled by said unit for opening/closing the connection;
a sensor, and
means for evacuating the gas present in the auxiliary container controlled by said unit.

Preferably the means for evacuating can comprise
gas venting means for venting the volume and/or the auxiliary container (the advantage is to move the gas in a natural and economic manner, for example by pressure difference), and/or
a deformable volume or chamber (preferably of known dimensions), e.g. a bag or membrane, in which the generated gas can migrate to then determine the amount thereof.

In particular, when wanting to sample periodically said amount and/or reduce the number and the size of the volumes for the generated gas, said unit can be adapted to
detect the attainment of a threshold of maximum pressure by reading the sensor(s) for detecting;
operate the means for evacuating in order to obtain a specific decrease of pressure,
process the value of said decrease to calculate said amount, e.g. the moles of evacuated gas.

The pressure transducer preferably
has precision of at least +/−10 mbar, and/or
is positioned in the upper part of the container (e.g. in a hatch or on the roof of the container) and/or in the auxiliary container.

Preferably, said unit can also control the normal functions in conventional fermenters (temperature control, pumps for pumping-over, blades for marc extraction, injections of gas mixtures for macro-oxygenation and soft breakage of marc cap, etc.).

Preferably the fermenter comprises means for detecting, e.g. a level probe (preferably controlled by said unit), adapted to detect a maximum level of material inside the container.

Said estimate of the total gas producible by the material is acquirable or calculated by the unit by using e.g. means or a sensor or a level sensor for detecting the amount of material (e.g. liquid+peel) loaded into the fermenter. From the amount of loaded material the unit can calculate, by knowing the internal capacity of the fermenter to which it is associated, the volume.

Figure 2:
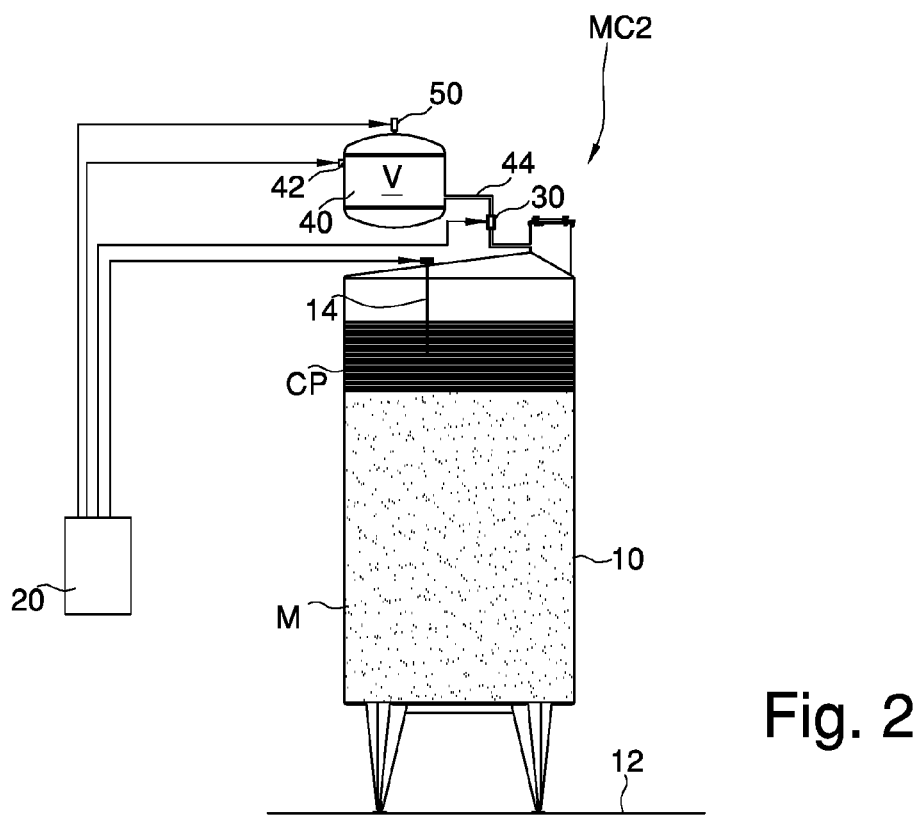

The advantages of the invention will be more apparent from the following description of a preferred embodiment, making reference to the attached drawing in which FIG. 1 shows a front view of an improved fermenter;

FIG. 2 shows a front view of a variant of the improved fermenter.

In the figures the (optional) pockets or means for thermoregulation and the respective detection temperature probes have not been shown. In the figures, same numerals indicate equal parts.

In FIG. 1 is shown a closed fermenter MC which includes a tank 10 for containing must M.

The tank 10 is equipped with
a level probe 14, adapted for measuring the level of liquid inside the tank 10;
a valve 16 for adjusting the gas pressure inside the tank 10;
a pressure sensor or transducer 18 capable of detecting the gas pressure inside the tank 10, and
an electronic control panel 20 or in general a programmable processing unit.

The tank 10 is filled with crushed material up to a maximum level allowed by the probe 14. In this way one is able to know exactly what is the void volume V (i.e. not occupied by the crushed grapes, i.e. liquid part+peel) of the tank 10.

We have $V=V_{tank}-V_{load}$, where
V is the empty volume of the tank 10 (measured e.g. by another sensor, not shown),
$V_{tank}$ is the volume of the entire tank 10, a given data, and
$V_{load}$ is the volume of the loaded crushed material, a data known during processing.

The unit 20, e.g. through a suitable software, is able to manage the reading of the sensors and the control of the valves on the tank 10. Via the unit 20, the method may be performed automatically. The arrows in the figure indicate control connections. In the following each action of the components of each fermenter are meant to be obtained via the control program of unit 20.

After the alcoholic fermentation has started, a cap CP forms, generated by the production of $CO_2$ which pushes upwards the skins. The cap CP emerges from the liquid must M by about 50% of its volume.

The floating part of the cap CP is made of the wet skins of must M and void spaces between peel and peel occupied by gas, which for a started fermentation is $CO_2$.

The volume occupied by the liquid mass (must) and by the solid part (peel) is the same as that occupied overall by the crushed material just loaded into the tank 10 when skins and liquid are mixed together.

Therefore, the measurement of the loaded crushed material is to be trusted to measure, by difference, the exact actual void volume V of the tank 10 even during the alcoholic fermentation, when the floating cap CP seems to reduce the actual void volume.

As already mentioned, to achieve control of the fermentation, the starting values may be two:

a. the amount of must (liquid) normally present in the crushed loaded material, and b. his sugar level.

The amount of must depends on the type of crushed grapes, and may be a data known with approximation of e.g. 5% by the oenologist (based on the initial analysis of the crushed grapes).

The sugar content of the grapes is measured before pressing the grapes or at the time of filling the tank 10 and is a trusted value, e.g. with a margin of error of 3%.

The unit 20 correlates the data derived from said sensors and the said two values a), b), and uses them to perform calculations in order to estimate the amount of $CO_2$ produced, using the data of void volume V and setting a maximum threshold pressure $P_{max}$ to be reached in the tank 10 by the $CO_2$ (e.g. 500 mbar). The pressures shown are relative to atmospheric pressure.

In fact the method of fermentation control can be based on the measurement of this quantity.

Operation

After reaching the maximum pressure $P_{max}$, detected by the sensor 18, tank 10 is depressurized by opening the valve 16 to obtain a certain pressure drop $\nabla P$ (e.g. 100 mbar).

Assuming, with good approximation, that the fermentation gases and $CO_2$ behave as ideal gases, and that the temperature does not vary substantially (temperature around 20° C. with relative pressures normally between 0 and 8 bar, conditions that meet very well the hypothesis of gas ideality). Starting from the ideal gas law:

$$P*V=N*R*T,$$

where:

P=pressure,
N=number of moles,
R=universal gas constant,
T=temperature in the volume, rearranging the formula we have:

$$N=P*V/R*T,$$

where, substituting to N and P the values of moles and pressure obtained, respectively, at the maximum pressure and at the residual pressure after the pressure drop $\nabla P$, we obtain:

$$N_{max}=V*P_{max}/R*T, \text{ and } N_{min}=V*P_{min}/R*T$$

where:

$N_{max}$=moles in the tank at the maximum pressure,
$N_{min}$=moles in the tank at the residual pressure after the pressure drop $\nabla P$,
$P_{max}$=maximum pressure in the tank before the pressure drop ($P_{max}>P_{min}$),
$P_{min}$=minimum pressure in the tank after the pressure drop $\nabla P$ ($P_{min}>0$ relative bar).

At this point, the number of moles $\nabla N$ at each pressure drop $\nabla P$ will be:

$$\nabla N=N_{max}-N_{min},$$

from which by working the formula and remembering that $\nabla P=P_{max}-P_{min}$ and $\eta$=corrective coefficient, we get:

$$\nabla N=(V*\nabla P*\eta)/(R*T) \quad (1)$$

i.e. the moles of gas ejected at each pressure drop $\nabla P$. To such $\nabla N$ corresponds a volume $V_{CO2}$ of $CO_2$ at standard atmospheric pressure $P_{atm}$ (1 bar) calculatable by rearranging the formula of ideal gases in the form:

$$V=N*R*T/P,$$

obtaining the following:

$$V_{CO2}=\nabla N*R*T/P_{atm}=V*\nabla P*\eta/P_{atm}. \quad (2)$$

The equations (1) and (2) constitute the samples of the amount of gas to be measured.

It is noted that $\eta$ is a corrective coefficient, e.g. of 5% (1.05), which takes into account the effect of stripping of $CO_2$ accumulated in the must due to the pressure (Henry's law) which occurs at each depressurization of a tank containing a fermenting mass. Experimental tests have shown that this value is however variable and correlated to the density of the must, the value of pressurization $P_{max}$, and the thickness and permeability of the cap CP. The unit can be programmed so that the value of the correction coefficient is configurable, to make it suitable to the type of grapes to process.

The electronic unit 20 carries out the calculation of equations (1) and/or (2), and can store it and/or add it to the data acquired and calculated during the previous de-pressurizations. By knowing the amount of $CO_2$ produced up to the last depressurization and correlating this data with the volume of must loaded into the tank 10 and the initial level of the sugars, one can know the stage at which the fermentation has come.

With the unit 20, based on the detected stage of fermentation, it is possible to set fermentation programs that can intervene on the mass inside the tank 10 with e.g. steps of or means for:

macro-/micro-oxygenation, and/or
injection of gas and/or $O_2$ from the outside,
adjustment of the temperature of the fermentation by thermoregulation interspaces; and/or
fermentation pressures, and/or
gas injections for mixing the must M and breaking the cap CP; and/or
pumping-overs, and/or
pressings, and/or
delestages, and/or
management of the timing of the interventions (and/or management of the interventions automated) on the fermentation mass by the aenologist, for example addition of yeasts, enzymes, aliments for yeast, etc.

It is possible to perform a measurement of the amount of $CO_2$ produced in the tank 10 at regular time intervals, comprised e.g. between 5 minutes and 2 hours. The sampling times (see equations (1) or (2)) may vary in relation to the stage reached by the alcoholic fermentation and/or be linked to the achievement of a maximum pressure in the known or deformable volume.

At the beginning and end of the fermentation, when the production of $CO_2$ is limited, the reaching in the tank 10 of the pressure $P_{max}$ is slower, while in the central phase of fermentation the $CO_2$ produced is remarkable and the pressure $P_{max}$ is reached very quickly.

By thickening the sampling of generated gas during the period of greatest production can detect with high accuracy the actual state of fermentation.

To make the measurement of the quantity $\nabla N$ and/or $V_{CO2}$ more precise, a further apparatus can be arranged on the tank 10 (FIG. 2, fermenter MC2), that allows eliminating the correction factor $\eta$.

To the tank 10 is added a second tank or variable volume 40, e.g. smaller and/or located on top of, beside or below the tank 10.

The tank 40 can also be accomplished as internal partition of the tank 10.

The fermenter MC2 comprises in addition:
- a connection pipe or conduit 44 between the tank 10 and the tank or variable volume 40;
- a valve 30 regulating the gas flow in the tube or conduit 44;
- a degassing valve 50;
- a pressure sensor or transducer 42 located on the tank or variable volume 40.

As previously, the unit 20 controls and adjusts each device of the fermenter MC2 (see arrows).

During the pressurization phase, the valve 30 is open, and the tank or variable volume 40 and the empty part of the tank 10 are pressurized simultaneously and isobarically by the fermentation $CO_2$.

At the desired pressure $P_{max}$, e.g. 500 mbar, the valve 30 is closed, and only the variable volume or tank 40 is degassed until the internal pressure, measured by the sensor 46, drops by $\nabla P$ (e.g. again 100 mbar).

Reached the lower limit of pressure (400 mbar in the example) in the tank 40 only, the valve 50 is closed and the valve 30 opens. The pressures between the tanks 10 and 40 balance and stripping of the gas contained in the must is distributed in the tank 40 and in the empty part V of the tank 10.

The cycle can be repeated whenever the upper limit $P_{max}$ is reached.

Therefore, by the degassing only the variable volume or tank 40 it can be known precisely the amount of produced $CO_2$, because the volume to be used in the formula (1) or (2) is that of the tank or variable volume 40 but without the correction factor η, since the tank or variable volume 40 does not contain any fermenting mass but uniquely $CO_2$.

In the fermenter MC2 the unit 20 works as described for the fermenter MC.

The invention claimed is:

1. A method comprising the steps of:
providing a fermenter comprising:
   a container for containing an organic material that can generate fermentation gas;
   a volume for containing gas generated from the material; and
   a detector configured to detect the amount of gas actually generated over time by the material in the volume; and
using an electronic processing unit to calculate progress in fermentation of the material contained in the container, comprising the sub-steps of:
measuring by said detector the amount of gas actually generated over time by the material, said amount being measured as a sum of measured doses of generated gas, wherein a dose is measured by making the generated gas:
   (i) reach in a known volume a threshold of maximum pressure; and/or
   (ii) invade a deformable volume;
determining the state of fermentation progress by comparing said amount with an estimate of the total gas producible by material throughout its fermentation; and
adjusting the fermentation progress based on the step of determining,
wherein in the known and/or deformable volume, a reduction of gas pressure is accomplished by moving elsewhere or taking away part of or all of the generated gas, and said dose is calculated as a function of said reduction.

2. The method according to claim 1, wherein said estimation is calculated as a function of the quantity of material in the container and/or its level of sugar.

3. The method according to claim 1, wherein the known and/or deformable volume is temporarily isolated from the container, and then gas is evacuated from the known and/or deformable volume.

4. The method according to claim 1, wherein the electronic processing unit is programmed to perform a series of programmed corrective actions by driving
   thermoregulation means to vary the temperature of the fermenting material in order to bring the actual fermentation closer to a desired, ideal fermentation curve, and/or
   means for performing pumping-overs, and/or
   means for oxygenating the material, and/or
   means for pressing the material.

5. The method according to claim 1, wherein the electronic processing unit is programmed to intervene on the mass inside the tank by driving means for:
   macro-/micro-oxygenation, and/or
   injection of gas and/or $O_2$ from the outside,
   adjustment of the temperature of the fermentation by thermoregulation interspaces; and/or fermentation pressures, and/or
   gas injections for mixing must (M) and breaking a cap (CP); and/or
   making pumping-overs.

6. A fermenter, comprising:
   a container for containing an organic material that can generate gas by fermentation; and
   a volume for containing gas generated from the material, comprising:
      a sensor configured to detect the gas pressure in the volume;
      a detector configured to detect an amount of gas actually generated over time by the material in the volume;
      a device configured to evacuate gas present in the volume; and
      an electronic processor configured to control the sensor and the device in order to evacuate from the volume known gas doses, and sum numerical values corresponding to the moles of gas of all the doses to obtain said amount.

7. The fermenter according to claim 6, wherein said volume comprises an auxiliary container for containing only gas, and wherein, controlled by said control unit, there are:
   a gas connection between the auxiliary container and said volume;
   a device configured to open/close the connection;
   a sensor for detecting the gas pressure in the auxiliary container; and
   an evacuator configured to evacuate gas present in the auxiliary container.

8. The fermenter according to claim 6, wherein said processor is adapted to:
   detect the attainment of a threshold of maximum pressure by polling a sensor for detecting;
   operate the evacuator so as to obtain a given reduction in pressure; and process the value of said reduction for calculating said dose, e.g. the moles of evacuated gas.

9. The fermenter according to claim 6, wherein the electronic processor is programmed to perform a series of programmed corrective actions by driving
- thermoregulation means to vary the temperature of the fermenting material in order to bring the actual fermentation closer to a desired, ideal fermentation curve, and/or
- means for performing pumping-overs, and/or
- means for oxygenating the material, and/or
- means for pressing the material.

10. The fermenter according to claim 6, wherein the electronic processor is programmed to intervene on the mass inside the tank by driving means for:
- macro-/micro-oxygenation, and/or
- injection of gas and/or $O_2$ from the outside,
- adjustment of the temperature of the fermentation by thermoregulation interspaces; and/or fermentation pressures, and/or
- gas injections for mixing must (M) and breaking a cap (CP); and/or
- making pumping-overs.

* * * * *